United States Patent [19]

Forrest et al.

[11] Patent Number: 5,065,739
[45] Date of Patent: Nov. 19, 1991

[54] RETRACTOR SUPPORT ASSEMBLY

[76] Inventors: William J. Forrest, 3400 NW. Expressway, Oklahoma City, Okla. 73112; Lewis C. Taylor, 1605 Norwood Pl., Oklahoma City, Okla. 73120

[21] Appl. No.: 398,169
[22] Filed: Aug. 24, 1989
[51] Int. Cl.$^5$ .............................................. A61B 17/02
[52] U.S. Cl. ...................................................... 128/20
[58] Field of Search ..................... 128/20, 400, 17, 18; 269/328

[56] References Cited

U.S. PATENT DOCUMENTS

| | | | |
|---|---|---|---|
| 3,196,865 | 7/1965 | Rose | 128/20 |
| 3,522,800 | 8/1970 | Lesser | 128/20 |
| 3,643,655 | 2/1972 | Peronti | 128/20 |
| 3,710,783 | 1/1973 | Jascalevich | 128/20 |
| 4,254,763 | 3/1981 | McCready et al. | 128/20 |
| 4,622,955 | 11/1986 | Fakhrai | 128/20 |

FOREIGN PATENT DOCUMENTS

| | | | |
|---|---|---|---|
| 690530 | 6/1930 | France | 128/20 |
| 8906111 | 7/1989 | PCT Int'l Appl. | 128/20 |
| 1210800 | 2/1986 | U.S.S.R. | 128/20 |

Primary Examiner—Edward M. Coven
Assistant Examiner—Mark S. Graham
Attorney, Agent, or Firm—Dunlap, Codding, Peterson & Lee

[57] ABSTRACT

A retractor support assembly for assisting a surgeon by supporting a portion of a breast of a patient during reconstructive surgery. The retractor support assembly includes a retractor having a blade which is insertable into a wound generally under a portion of the breast whereby a portion of the breast is supported generally on the blade. The retractor support assembly also includes a retractor support connected to the retractor for exerting a predetermined force on the retractor pulling the retractor a predetermined distance in a generally upwardly direction whereby the portion of the breast supported on the blade of the retractor is lifted and moved in the generally upwardly direction the predetermined distance toward a breast lifted position. The retractor support supports the retractor and the portion of the breast supported on the retractor in the breast lifted position during the reconstructive surgery.

9 Claims, 5 Drawing Sheets

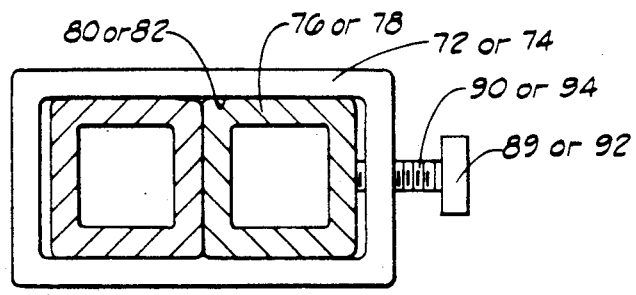
FIG. 4
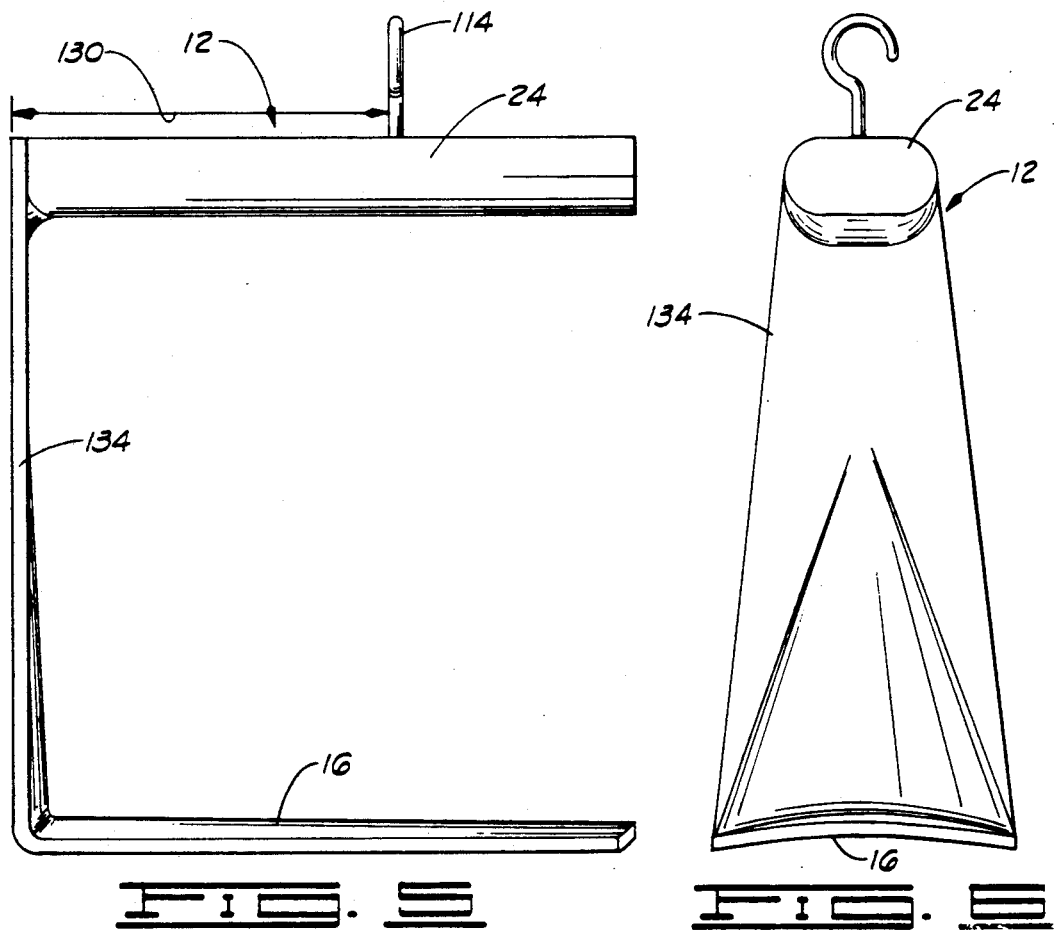
FIG. 5
FIG. 6
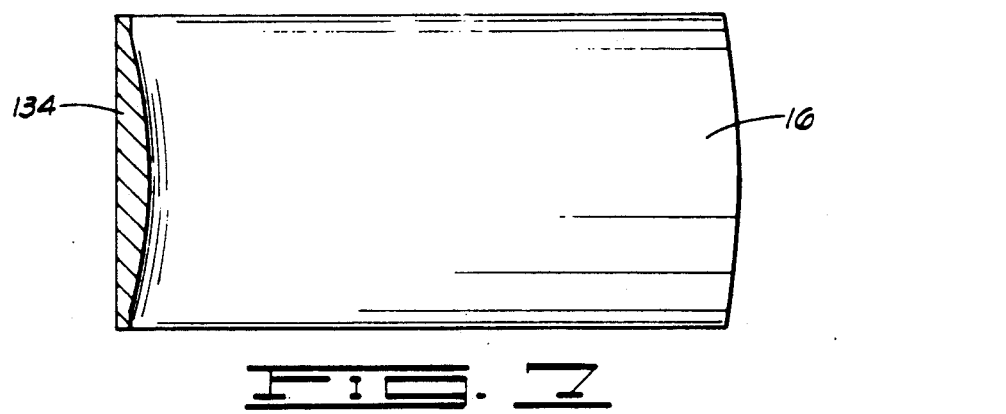
FIG. 7

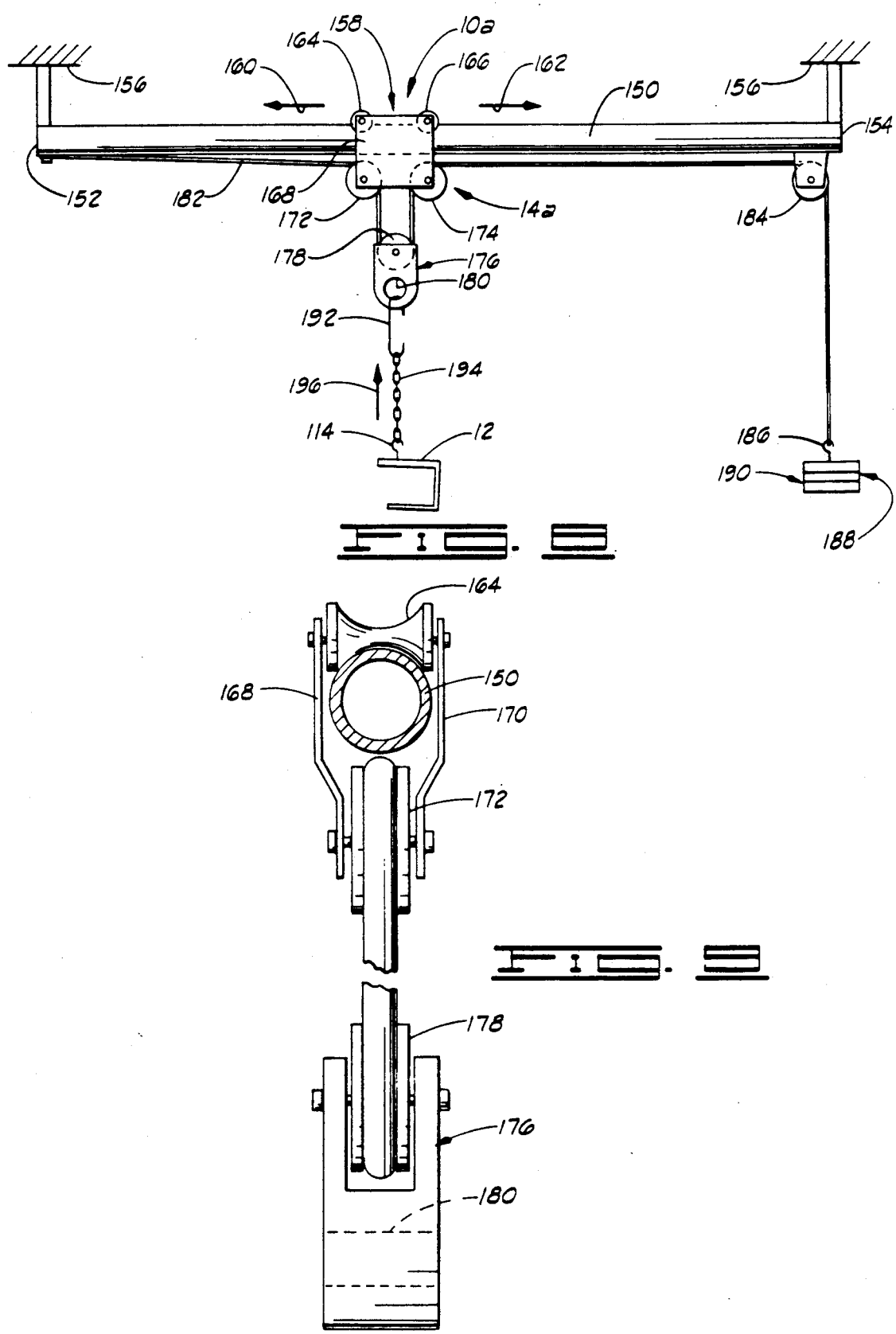

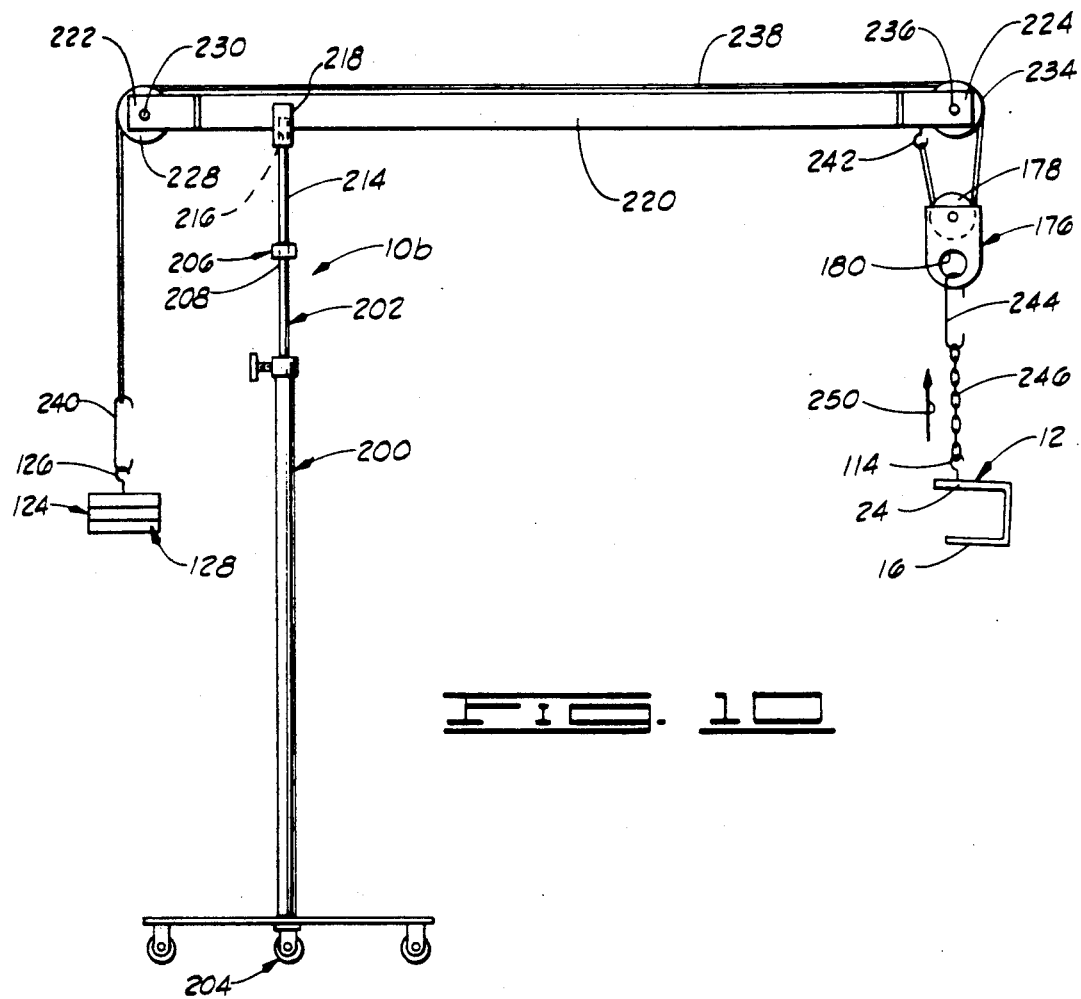
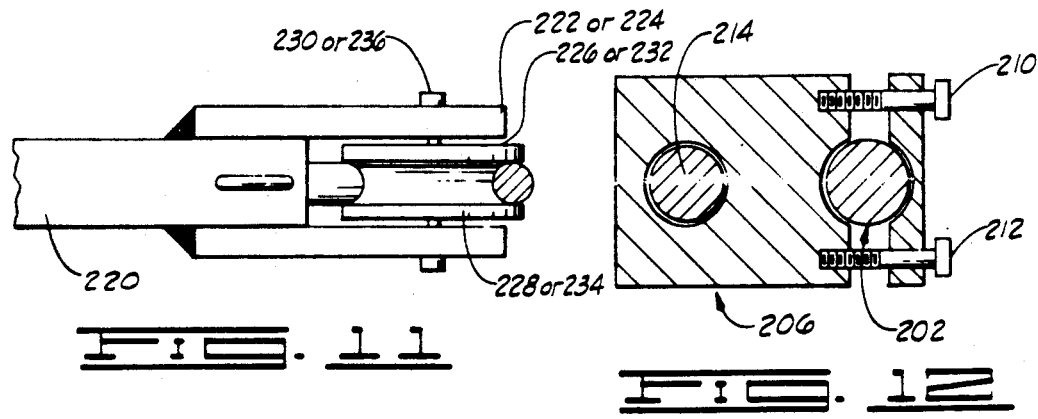

RETRACTOR SUPPORT ASSEMBLY

FIELD OF THE INVENTION

The present invention relates generally to a device for supporting a portion of a breast of a patient in a breast lifted position during reconstructive surgery.

BRIEF DESCRIPTION OF THE DRAWINGS

FIG. 4 is a sectional view showing a portion of the connection of the retractor support assembly to the table.

FIG. 5 is a side elevational view of a retractor of the retractor support assembly of FIG. 1.

FIG. 6 is an end elevational view of the retractor of FIG. 5.

FIG. 7 is a top elevational view of the blade of the retractor of FIGS. 5 and 6.

FIG. 8 is a side elevational view of a modified retractor support assembly.

FIG. 9 is a front elevational view, partial sectional view of a portion of the retractor support assembly of FIG. 8.

FIG. 10 is a side elevational view of another modified retractor support assembly supported on an IV stand.

FIG. 11 is a top elevational view of a portion of the modified retractor support assembly of FIG. 10.

FIG. 12 is a front elevational view of the block of the modified retractor support assembly shown in FIG. 10.

DESCRIPTION OF THE PREFERRED EMBODIMENTS

Mammary glands lie over the pectoralis major and serratus anterior muscle and the mammary glands are attached to the muscle via a layer of connective tissue. In breast surgery particular augmentation mammoplasty, an incision is made generally under the breast and the surgeon cuttingly separates the breast from muscle so an implant can be disposed between the breast and the muscle. In this procedure, the surgeon inserts the blade of a retractor into the wound and the surgeon grips the handle of the retractor and physically lifts the retractor and the portion of the breast supported on the retractor blade. With the surgeon's free hand, the surgeon continues the procedure of cuttingly separating the breast from the muscle while holding the breast in a breast lifted position via the retractor. As the wound gets deeper, a different retractor with a longer blade is utilized.

Although the breast only weighs about 3 or 4 pounds, this type of surgery requires about one hour per breast. During this about two hour procedure, the surgeon is supporting the breast via the retractor and maneuvering the retractor to better expose portions of the wound. This is a long and tiring procedure and, during this procedure, a great deal of stress and strain is placed on the surgeon's arm and elbow.

Figure 1:
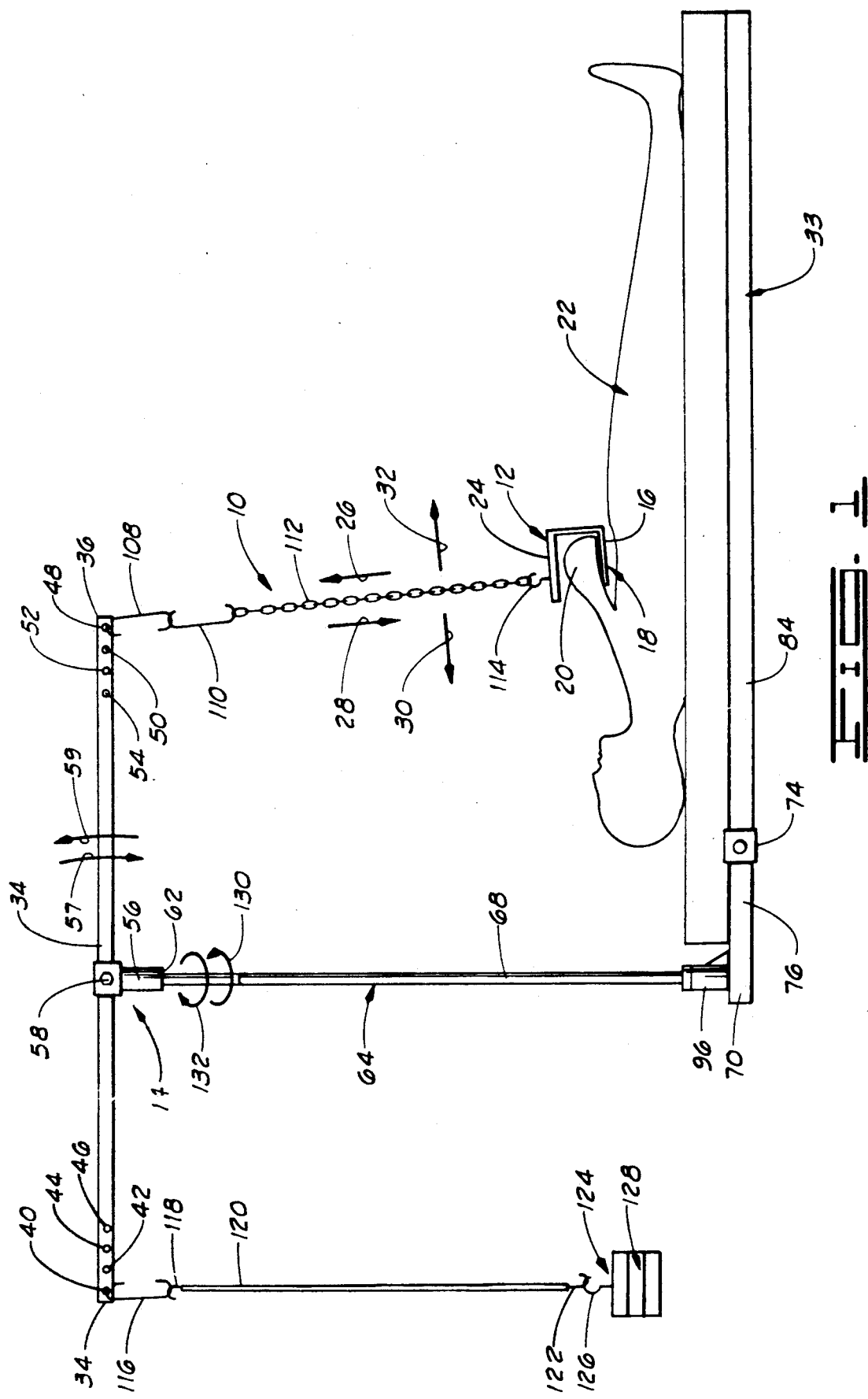
FIG. 1 is a side elevational, diagrammatic view of a retractor support assembly constructed in accordance with the present invention and removably attached to a table, a patient being diagrammatically shown in FIG. 1 lying on the upper surface of the table with a portion of the retractor support assembly supporting a breast of the patient in a breast lifted position.

A retractor support assembly constructed in accordance with the present invention is shown in FIG. 1 and designated therein by the general reference numeral 10. The retractor support assembly 10 comprises a retractor 12 and a retractor support 14.

The retractor 12 has a blade 16 which is insertable into a wound 18 and generally under a portion of a breast 20 of a patient 22. The retractor 12 also includes a handle 24 which is connected to the blade 16.

The retractor support 14 is connected to the handle 24 of the retractor 12. The retractor support 14 exerts a predetermined force on the retractor 12 tending to pull the retractor 12 a predetermined distance in a generally upwardly direction 26 thereby lifting the portion of the breast 20 supported on the blade 16 of the retractor 12 in the generally upwardly direction 26. The blade 16 and the portion of the breast 20 supported on the blade 16 is moved in the generally upwardly direction 26 toward a breast lifted position, the retractor 12 being shown in FIG. 1 supporting a portion of the breast 20 in the breast lifted position.

The retractor support 14 supports the breast 20 in the breast lifted position. The retractor 12 is flexibly or maneuverably supported by the retractor support 14 so the surgeon can grip the handle 24 for maneuvering the handle 24 and the blade 16 connected thereto in the generally upwardly direction 26 or downwardly direction 28 or in a left direction 30 or in a right direction 32 or twist the handle 24 and the blade 16 connected thereto in the generally left or right direction 30 or 32 for moving the supported portion of the breast 20 in any desired direction while the breast 20 remains basically supported via the retractor support 14.

Figure 2:
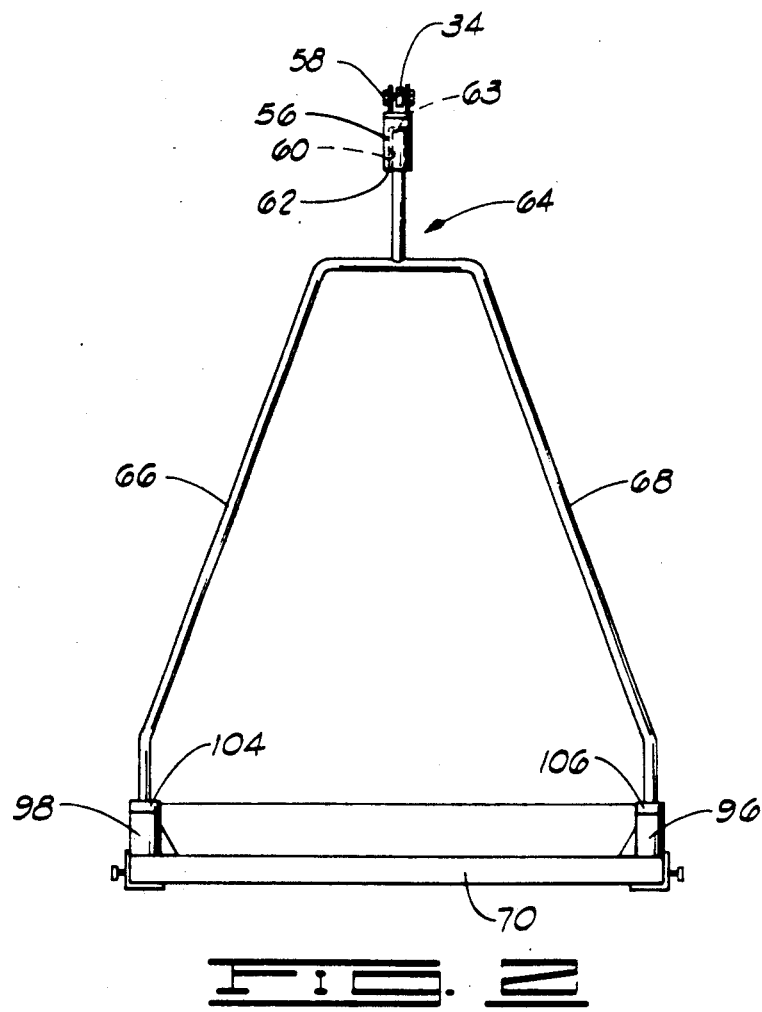
FIG. 2 is an end view showing a portion of the retractor support assembly of FIG. 1 illustrating the attachment of the retractor support assembly to the table.

The retractor support 14 provides about a vertical traction on the retractor 12 in a range from about 3 pounds to about 6 pounds. The amount of traction provided via the retractor support 14 is adjustable in a manner to be made more apparent below. The retractor support 14 exerts a relatively constant traction regardless of the position of the retractor 12. While maintaining traction on the retractor 12, the retractor 12 stills remains in the wound 18 without the surgeon or the surgeon's assistance having to holdingly support the retractor 12 and the portion of the breast 20 supported thereon. The retractor support 14 also is adapted so the surgeon can utilize the retractor support 14 for supporting the retractor 12 and the portion of the breast 20 supported thereon in the breast lifted position while working on the left breast and then move the retractor support 14 for using the retractor support 14 for supporting the right breast in the breast lifted position. The retractor support 14 provides adequate vertical travel regardless of the height of a table 33 (shown in FIG. 1). As shown in FIGS. 1 and 2, the retractor support 14 comprises a rocking arm 34 having a first end 36 and a second end 38. A plurality of spaced apart holes are formed in the rocking arm 34 generally near the first end 36 thereof (four holes being shown in FIG. 1 and designated therein by the reference numerals 40, 42, 44 and 46). A plurality of holes are formed in the rocking arm 34 generally near the second end 38 thereof (four holes being shown in FIG. 1 and designated therein by the reference numerals 48, 50, 52 and 54). The holes 40, 42, 44 and 46 are spaced a distance apart generally along the length of the rocking arm 34. The holes 48, 50, 52 and 54 also are spaced a distance apart generally along the length of the rocking arm 34.

As shown in FIGS. 1 and 2, a portion of a pivot holder 56 is pivotingly connected to the rocking arm 34 via a pivot pin 58 at a position generally between the opposite ends 36 and 38 of the rocking arm 34. A portion of the pivot holder 56 is tubular shaped and has an opening 60 (FIG. 2) extending a distance therethrough and intersecting an end 62 thereof. The rocking arm 34 is pivotally movable about the pivot connection provided via the pivot pin 58 in a direction 57 or a direction 59.

An end 63 (FIG. 2) of a vertical frame 64 is slidingly disposed in the opening 60 in the pivot holder 56 for removably connecting the vertical frame 64 to the pivot holder 56. As shown more clearly in FIG. 2, the lower end of the vertical frame 64 is generally Y-shaped thereby forming a first leg 66 and a second leg 68.

As shown in FIGS. 1, 2, 3 and 4, an extension bar 70 is connected to the table 33 via clamps 72 and 74. More particularly, a side rail 76 (FIGS. 1 and 3) is connected to one end of the extension bar 70 and another side rail 78 (FIG. 3) is connected to the opposite end of the extension bar 70. The clamps 72 and 74 each are generally square shaped and each clamp 72 and 74 has an opening 80 and 82 (FIG. 4), respectively, extending therethrough and intersecting opposite ends thereof. The rail 76 extends through the opening 82 in the clamp 74 and the rail 78 extends through the opening 80 in the clamp 72. The rail 76 is disposed generally adjacent a frame member 84 (FIG. 4) on the table 33 and positioned so that the frame member 84 also extends through the opening 82 in the clamp 74. The rail 78 is disposed generally adjacent a frame member 86 (FIG. 4) on the table 33 and positioned so that the frame member 86 also extends through the opening 90 in the clamp 72. The rail members 76 and 78 are slidingly adjusted with respect to the frame members 84 and 86 to position the vertical frame 64 in a predetermined position. When the rails 76 and 78 are in the desired position, a hand wheel 88 on the clamp 72 is rotated for moving a screw locking member 90 against the rail 78 for clamping the rail 78 to the frame member 86 and a hand wheel 92 is rotated to move a screw locking member 94 into engagement with the rail 76 for locking the rail 76 to the frame member 84.

Figure 3:
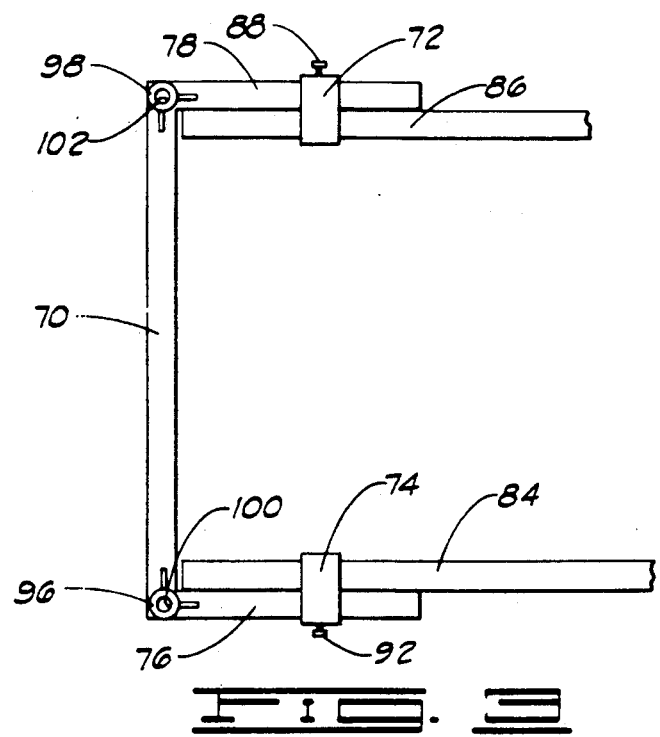
FIG. 3 is a plan showing a portion of the table and a portion of there tractor support assembly for attaching the retractor support assembly to the table.

As shown in FIGS. 2 and 3, a support post 96 is secured generally to one end of the extension bar 70 and another support post 98 is secured to the opposite end of the extension bar 70. Each of the support post 96 and 98 extends a distance in a generally upwardly direction. The support post 96 has an opening 100 (FIG. 3) extending a distance therethrough and intersecting one end thereof and the support post 98 has an opening 102 (FIG. 3) extending a distance therethrough and intersecting one end thereof. One end of the first leg 66 is slidingly disposed in the opening 102 in the support post 98 and one end of the second leg 68 is slidingly disposed in the opening 100 of the support post 96 for removably connecting the vertical frame 64 to the table 33. A stop 104 (FIG. 2) is secured to the first leg 66 and the stop 104 is positioned to engage one end of the support post 98 for positioning the first leg 66 in the opening 102 of the support post 98. A stop 106 is secured to the second leg 68 and positioned to engage one end of the support post 96 for positioning the second leg 68 in the opening 100 of the support post 96.

As shown in FIG. 1, one end of a U-shaped front clevis 108 is hooked through the hole 49 in the rocking arm 34. The opposite end of the front clevis 108 is hooked through one end of a front hook 110. The opposite end of the front hook 110 is secured to one end of a chain 112. The opposite end of the chain 112 is secured to a retractor hook 114 which is connected to the handle 24 of the retractor 12.

One end of a rear clevis 116 is secured through the hole 48 in the rocking arm 14. The opposite end of the rear clevis 116 is connected to a hook 118 formed on one end of a rod 120. A hook 122 is formed on the opposite end of the rod 120.

A weight support 124 is connected to the opposite end of the rod 120. More particularly, a hook 126 is secured to the weight support 124 and the hook 126 is connected to the hook 122 for securing the weight support 124 to the end of the rod 120. A plurality of weights 128 are secured in the weight support 124. In one form, as shown in FIG. 1, three weights are supported on the weight support 124, two one pound weights and one three pound weight.

In operation, the surgeon inserts the blade 16 into the wound 18. The weights 128 force the second end 38 of the rocking arm 34 in the downward direction 28 thereby causing the rocking arm 34 to be pivotally moved in the direction 59 about the pivot pin 58. This movement of the rocking arm 34 in the direction 59 causes the retractor 12 to be moved in the generally upwardly direction 26 due to the connection between the rocking arm 34 and the retractor 12 provided via the front clevis 108, the front hook 110 and the chain 112. As the retractor 12 is moved in the generally upwardly direction 26, the portion of the breast 20 supported on the blade 16 is moved in the generally upwardly direction 26 to the breast lifted position, as shown in FIG. 1. The retractor support 14 supports the breast 20 in the breast lifted position. Since the retractor 12 is connected to the rocking arm 34 via the chain 112, the surgeon can grip the handle 24 and maneuver the portion of the breast 20 supported on the blade 16 by moving the handle in the upwardly direction 26 or the downwardly direction 28 or the left direction 30 or the right direction 32, as desired by the surgeon during operation.

The rocking arm 34 is also rotatably supported on the vertical frame 64 so that the rocking arm 34 can be rotated in a direction 130 or a direction 132 for positioning the retractor 12 under either the right or the left breast.

The retractor 12 is shown in greater detail in FIGS. 5, 6 and 7. As shown in FIGS. 5, 6 and 7, the retractor 12 includes the handle 24 which basically comprises a hollow tube having a generally oval shaped cross-section with both ends of the tube being closed. The retractor hook 114 is connected to the handle 24 at a position spaced a distance 130 from the end of the handle 34 connected to the blade 16. The distance 130 is about two-thirds of the entire length of the handle 24. The blade 16 is curved in one cross-section as shown in FIGS. 6 and 7 and the end of the blade 16 also is formed on a curved path. One end of the blade 16 is connected a blade extension 134 and the opposite end of the blade extension 134 is connected to one end of the handle 24. The blade 16, the blade extension 134 and the handle 24 form a generally U-shape retractor 12 with the handle 24 extended in a plane about parallel with the planar disposition of the blade 16. The blade extension 134 is curved with a curvature varying so that the end of the blade extension 134 which is connected to one end of the handle 24 virtually is not curved. The width of the blade extension 134 varies from the width of the blade 16 to the width of the end of the handle 24 which is connected to the blade extension 134.

EMBODIMENTS OF FIGS. 8 AND 9

Shown in FIGS. 8 and 9 is a modified retractor support assembly 10a the modified retractor support assembly 10a includes a modified retractor support 14a which is adapted to support the retractor 12 in a manner and for reasons like that described before with respect to the retractor support assembly 10.

The retractor support 14a includes a trolley tube 150 having opposite ends 152 and 154. The ends 152 and 154 are supported from a ceiling 156 so that the trolley tube 150 is supported a distance above the table and patient supported thereon.

A trolley 158 is rollingly supported on the trolley tube 150 for movement in a left direction 160 or a right direction 162 the trolley 158 basically comprises a pair of trolley wheels 164 and 166 rollingly connected to a pair of trolley frame members 168 and 170. The trolley frame members 168 and 170 are disposed on opposite sides of the trolley tube 150. The trolley wheels 164 and 166 are disposed generally on the upper surface of the trolley tube 150.

A pair of pulleys 172 and 174 are rollingly supported on the trolley frame members 168 and 170. The pulleys 172 and 174 are disposed generally below the trolley tube 150. The retractor support 14a also includes a block 176 having a pulley 178 rollingly connected to the block 176. A block opening 180 is formed through a lower portion of the block 176.

One end of a cable 182 is secured to the trolley tube 150 generally near the end 152 thereof. The cable 182 is extended over the pulley 172, extended about the pulley 178 and over the pulley 174. The cable 182 is extended from the pulley 174 over a weight pulley 184 which is rollingly supported on the trolley tube 150 generally near the end 154 thereof. The cable 182 is extended from the pulley 184 and the end of the cable 182 is secured to a hook 186 of a weight support 188. A plurality of weights 190 are supported in the weight support 188.

One end of a hook 192 is hookingly secured through the block opening 180 of the block 176. One end of a chain 194 is secured to the opposite end of the hook 192 and the opposite end of the chain 194 is secured to the retractor hook 114 of the retractor 12.

In operation, the weights 190 pull on the cable 182 thereby causing a force to be applied to the retractor 12 in a generally upwardly direction 196 for maintaining traction on the retractor 12 in a manner and for reasons like that described before with respect to the retractor support assembly 10 and the retractor 12. The position of the retractor 12 with respect to the trolley tube 150 can be varied by moving the trolley 158 in the left or right directions 160 or 162 to position the retractor 12 in the proper position with respect to the patient.

It should be noted, although the modified retractor support assembly 10a has been shown in FIGS. 6 and 7 as being supported from a ceiling, the retractor support assembly 10a could be supported on the table 33 using a modified vertical frame adapted to be connected to the opposite ends 152 and 154 of the retractor support assembly 10a.

EMBODIMENTS OF FIGS. 10, 11 AND 12

Shown in FIGS. 10, 11 and 12 is another modified retractor support assembly 10b. The retractor support assembly 10b particularly is adapted to be supported on a stand 200 which comprises a post 202 rollingly supported on wheels 204.

One end of a post extension 206 is disposed generally about and on opposite sides of the post 202 generally near an upper end 208 of the post 202 and the post extension 206 is secured to the post 202 via a pair of clamp screws 210 and 212. The post extension 206 extends a distance generally perpendicularly from the post 202 and a rod 214 is connected to the post extension 206. The rod 214 extends a distance generally upwardly from the post extension 206.

The rod 214 is slidingly disposed in an opening 216 of a tube 218. The opposite end of the tube 218 is secured to a bar 220 at a position generally between opposite ends 222 and 224 of the bar 220.

An opening 226 is provided in the end 222 of the bar 220 and a pulley 228 is disposed in the opening 226 and rollingly supported therein via a pin 230.

An opening 232 is formed in the end 224 of the bar 220 and a pulley 234 is disposed in the opening 232. The pulley 234 is rollingly supported in the opening 232 via a pin 236. A cable 238 extends over the pulley 228 and one end of the cable is connected to a hook 240. The opposite end of the hook 240 is hookingly connected to the hook 126 of the weight support 124. The weights 128 are supported in the weight support 124 in a manner exactly like that described before with respect to the weight support 124.

The cable 238 also extends over a portion of the pulley 236 and about the pulley 178 of the block 176 and the opposite end of the cable is secured to a hook 242, thereby securing the cable 238 to the bar 220. A hook 244 is connected to the block 176 and to a chain 246 with the chain 246 being connected to the retractor hook 114 on the retractor 12.

In operation, the weights 128 result in a force being applied to the retractor 12 in a generally upwardly direction 250 for maintaining a predetermined traction on the retractor 12 in the manner and for reasons exactly like that described before with respect to the retractor support assemblies 10 and 10a.

Although the modified retractor support assembly 10b has been described as being connected to the stand 200, it should be noted that the retractor support assembly 10 can be connected to the table 33 via the vertical frame 64 or modified version thereof in a manner like that described before with respect to the retractor support assembly 10 or it could be supported from the ceiling like the retractor support assembly 10a.

Changes may be made in the construction and the operation of the various embodiments of the retractor support assemblies described herein without departing from the spirit and scope of the invention as defined in the following claims.

What is claimed is:

1. A retractor support assembly for assisting a surgeon by supporting a portion of a breast of a patient during reconstructive surgery, comprising:
    a retractor having a blade which is insertable through a wound near the breast, the blade being insertable through the wound and under a portion of the breast; and a retractor support means connected to the blade of the retractor for exerting a predetermined force on the retractor tending to pull the retractor a predetermined distance in a generally upwardly direction for lifting the portion of the breast supported on the blade of the retractor and moving the blade and the portion of the breast supported on the blade in the generally upwardly direction the predetermined distance toward a breast lifted position, the retractor support means cooperating to maintain traction on the retractor for supporting the retractor and the portion of the breast supported on the blade of the retractor in the breast lifted position, comprising:

rocking arm means;

means for flexibly connecting the retractor to the rocking arm means whereby the blade of the retractor and the portion of the breast supported on the blade of the retractor are movable by the surgeon for lifting, lowering, moving in generally a left direction and moving in generally a right direction; and weight means supported on the rocking arm means for pulling the retractor in generally an upwardly direction and exerting the predetermined force on the retractor to pull the retractor and the portion of the breast supported on the blade of the retractor the predetermined distance in generally the upwardly direction toward the breast lifted position.

2. The retractor support assembly of claim 1 further comprising:

table means for supporting the patient and for movement in an upwardly direction and a downwardly direction during the reconstructive surgery; and wherein the retractor support assembly further comprises:

means for maintaining the position of the retractor relative to the patient as the table is moved in the generally upwardly direction or the generally downwardly direction.

3. The retractor support assembly of claim 1 including a table on which a patient is supported which is movable in an upwardly direction and a downwardly direction during the reconstructive surgery, and wherein the retractor support assembly further comprises:

means for connecting the retractor support means to the table for moving the retractor support means in the generally upwardly direction or the generally downwardly direction with the movement of the table and for maintaining the position of the retractor relative to the patient as the table is moved in the generally upwardly direction or the generally downwardly direction.

4. The retractor support assembly of claim 1 wherein the retractor further comprises:

a blade extension having opposite ends, one end of the blade extension being connected to one end of the blade and the blade extending substantially perpendicularly from the blade extension; and a handle having opposite ends with one end of the handle being connected to the end of the blade extension, opposite the end of the blade extension connected to the blade, the handle extending substantially perpendicularly from the blade extension and generally over the blade substantially parallel to the blade.

5. The retractor support assembly of claim 1 wherein the rocking arm means comprises:

a rocking arm having a first end and a second end; wherein the weight means is connected to the rocking arm generally near the first end of the rocking arm; and wherein the retractor is connected to the rocking arm generally near the second end of the rocking arm; and wherein the retractor support means further comprises:

a vertical frame having one end movably connected to the rocking arm at a position generally between the first and the second ends of the rocking arm for movably supporting the rocking arm generally above the patient, the rocking arm being movably supported on the vertical frame.

6. The retractor support assembly of claim 5 further comprising:

means for connecting the end of the vertical frame, opposite the end movably connected to the rocker arm, to the table.

7. The retractor support assembly of claim 5 wherein the vertical frame is movably connected to the rocking arm for pivotal movement of the arm in the generally upwardly direction and in the generally downwardly direction and for rotating movement in the generally left direction or in the generally right direction.

8. The retractor support assembly of claim 7 wherein the vertical frame further comprises:

a pivot holder movably connected to the rocking arm;

a tube having one end connected to the pivot holder with an opening extending through the tube and intersecting the end thereof opposite the end connected to the pivot holder:

a rod having one end disposed in the opening in the tube for slidingly and rotatingly connecting the tube to the rod; and means for supporting the rod and the rocking arm connected thereto at a position generally above the patient.

9. The retractor support assembly of claim 5 wherein the means for connecting the retractor to the rocking arm further comprises:

a chain having opposite ends with one end of the chain being connected to the retractor and the opposite end of the chain being connected to the rocking arm.

* * * * *